United States Patent
Hall et al.

(10) Patent No.: US 6,312,472 B1
(45) Date of Patent: Nov. 6, 2001

(54) BIOCOMPATIBLE MEDICAL IMPLANT ELEMENT

(75) Inventors: Jan Hall, Göteborg; Leif Hermansson, Uppsala, both of (SE)

(73) Assignee: Nobel Biocare AB, Göteborg (SE)

( * ) Notice: Subject to any disclaimer, the term of this patent is extended or adjusted under 35 U.S.C. 154(b) by 0 days.

(21) Appl. No.: 09/530,420

(22) PCT Filed: Oct. 28, 1998

(86) PCT No.: PCT/SE98/01948

§ 371 Date: Jul. 19, 2000

§ 102(e) Date: Jul. 19, 2000

(87) PCT Pub. No.: WO99/26673

PCT Pub. Date: Jun. 3, 1999

(30) Foreign Application Priority Data

Nov. 11, 1997 (SE) ..................................................... 9704115

(51) Int. Cl.[7] ....................................................... A61F 2/36
(52) U.S. Cl. ..................... 623/23.53; 623/23.56; 427/2
(58) Field of Search .............................. 623/23.53, 23.6, 623/23.61, 16.11; 433/201, 201.1; 427/2; 205/107, 322

(56) References Cited

U.S. PATENT DOCUMENTS

| | | | | |
|---|---|---|---|---|
| 4,497,629 | * | 2/1985 | Ogino | 433/201 |
| 4,702,930 | * | 10/1987 | Heide | 427/2 |
| 4,846,837 | * | 7/1989 | Kurze | 623/23.6 |
| 4,965,088 | * | 10/1990 | Shimamune | 623/23.53 |
| 5,139,424 | * | 8/1992 | Yli-Urpo | 433/201.1 |
| 5,211,833 | * | 5/1993 | Shirkhanzadeh | 205/322 |
| 5,609,633 | * | 3/1997 | Kokubo | 623/23.61 |
| 5,723,038 | * | 3/1998 | Scharnweber | 205/107 |
| 6,117,172 | * | 9/2000 | Ripamonti | 623/16.11 |

* cited by examiner

*Primary Examiner*—Dinh X. Nguyen
*Assistant Examiner*—Urmi Chattopadhyay
(74) *Attorney, Agent, or Firm*—Connolly Bove Lodge & Hutz, LLP

(57) ABSTRACT

The object of the invention is to make available implant elements or other medical products made of biological material with optimum mechanical and biological properties for a wide group of materials by introduction of a specially designed surface layer onto a strong core, where the surface layer is densified by means of hot isostatic pressing and dimensioned according to the basic fracture mechanics equation so that the thickness of the surface layer is less than c in the equation $K_{IC} = Y\sigma c^{1/2}$, where $K_{Ic}$ is the fracture toughness, Y a position and shape factor, c the critical defect size, and $\sigma$ the permitted stress for the actual material and the chosen design stress.

23 Claims, 2 Drawing Sheets

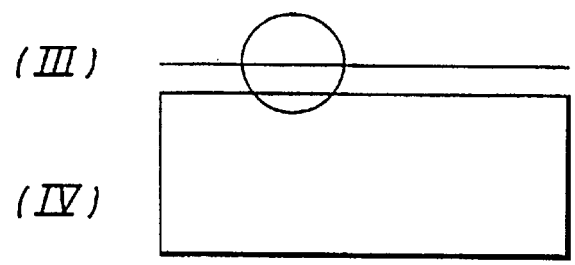
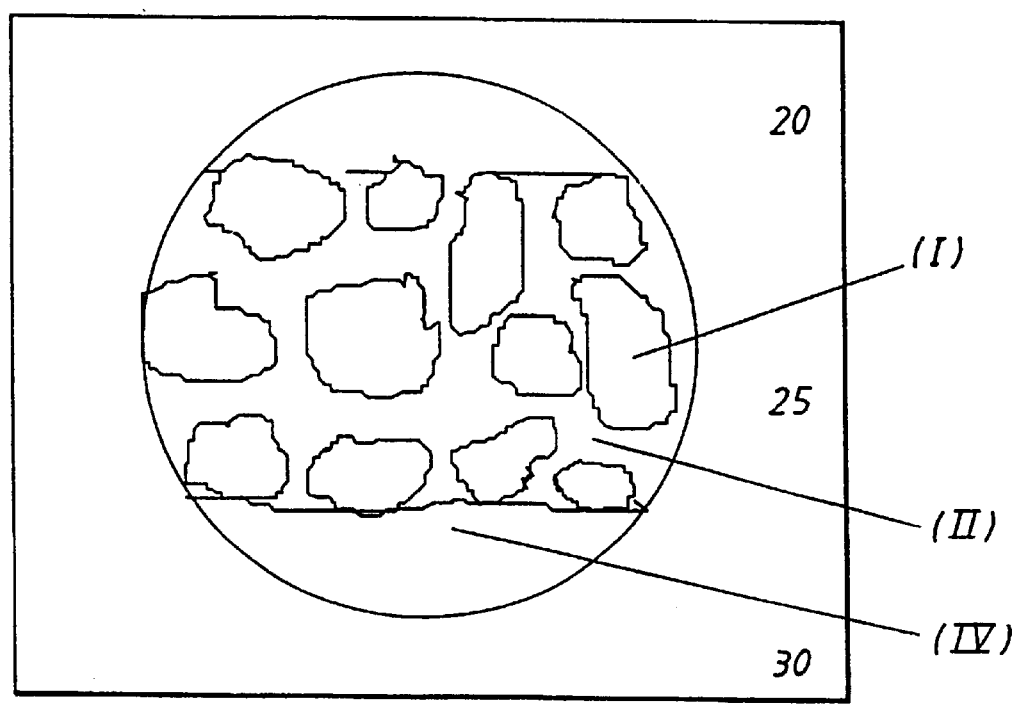

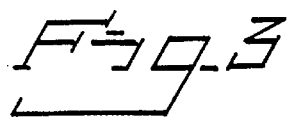
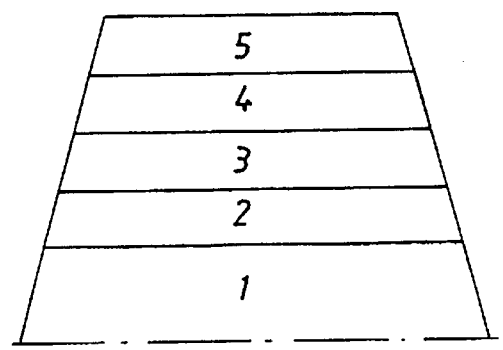
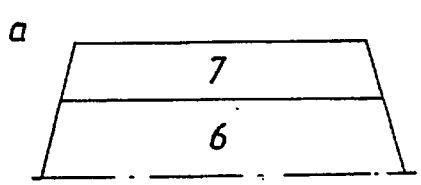
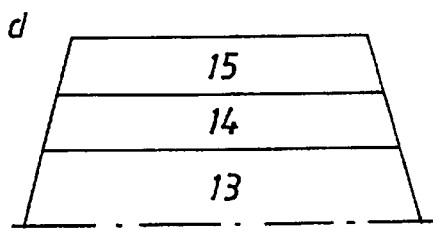
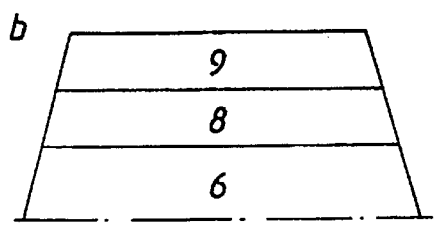
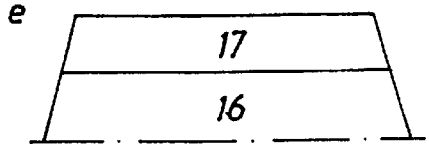
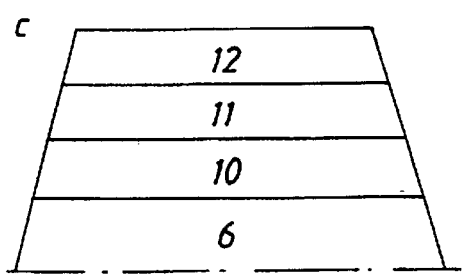
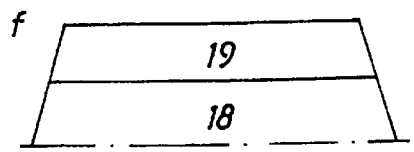

US 6,312,472 B1

BIOCOMPATIBLE MEDICAL IMPLANT ELEMENT

REFERENCE TO RELATED APPLICATION

This application is a 371 of PCT/SE98/01948, filed Oct. 28/1998.

TECHNICAL FIELD

The present invention relates to an implant element or other medical component made of a material consisting of a core and of a surface layer applied thereon, which has a high degree of strength and a favourable biological response to surrounding tissue.

BACKGROUND TO THE INVENTION

The material used in medical situations can consist of widely different groups of materials such as metals, polymers or ceramics. In such situations, materials are sought which are stable from the point of view of corrosion and erosion, and which have good strength characteristics in vivo. In addition to high mechanical and chemical stability, the material must exhibit good biocompatibility. For implants which are intended to support loads, it is also of great importance for the material to have good bone-anchoring ability by means of the contact zone between newly formed bone and implant exhibiting high shearing forces, i.e. high binding strength between implant and bone. Examples of materials with low load-bearing ability but with good anchoring in surrounding tissue are hydroxyapatite and fluoroapatite. In the presence of hydroxyapatite or biologically active glass (calcium phosphate-containing material) in the implant material, direct contact has been reported between bone tissue and implant at the atomic level (inter alia, Tracy and Doremus, J. Biomed. Mater. Res. Vol. 18, 719–726 (1984), and Hench, J. Am. Ceram. Soc., Vol. 74, page 1501 (1991)). However, a pure apatite phase or high content of apatite (in excess of 50% by volume) affords too little strength and a material which is inclined towards slow fissure growth (e.g. Metal and Ceramic Biomaterials, Vol. II, FIG. 5, page 52, CRC Press, 1982).

A combination of the aspects of strength and good anchoring ability is described in the patent literature by McGee, U.S. Pat. No. 3,787,900 (1974). The material here is a composite of spinel and Ca phosphate. However, the strength of such materials is relatively low. Combining increased strength and anchoring ability has previously been demonstrated by mixing apatite and a construction oxide, for example zirconium oxide, in a prescribed manner (Swedish Patent 465 571) and by densifying by means of hot isostatic pressing. In these materials, which are in the form of bulk materials—not surface layers as in the present invention—the Ca phosphate phase content is limited so as not to adversely affect the strength, as is explained by Experiment 2 in the text and Patent claim 5 in said Swedish Patent 465 571, where the Ca phosphate content is limited to 5–35 % by volume, preferably 10–25% by volume. This accords with general strength development upon introduction of a weaker phase, where the strength falls dramatically at contents in excess of about 20% by volume. For the zirconium oxide/hydroxyapatite system, the dependence of the strength on the apatite content is described in detail by Li et al. (Biomaterials Vol. 17, page 1789, FIG. 2, 1996).

A surface layer of Ca phosphate is an established technique for implants. A number of different methods for applying such surface layers are reported in the literature, such as wet chemical methods (e.g. sol-gel methods) with subsequent sintering, electrode deposition methods, plasma spraying and pulsed laser deposition, gas deposition methods (CVD and PVD) and hot isostatic pressing. Plasma spraying is generally used as the coating method. Use of hot isostatic pressing is reported in the literature for pure hydroxyapatite with layer thicknesses of 20–50 micrometres, i.e. considerably thicker than is envisaged in the present invention, and with problems in obtaining sufficient quality in terms of the micro-structure and strength of the surface layers, see Heide and Roth, Int. Conf. on Hot Isostatic Pressing, June 1987, and Herö et al., J. Biomed. Mater. Res., Vol. 28, 343–348, 1994.

With a biocompatible phase limited to a very thin surface layer having a specific maximum thickness calculated from the basic equation governing the fracture mechanics, it is possible, according to the invention, to increase the strength of the surface layer in such a way that this does not limit the strength of the component. This means that the optimum core can be chosen from the point of view of general design function, e.g. in terms of strength and in terms of machining (shaping), and that the optimum surface layer can be chosen from the point of view of biomaterials, i.e. biocompatible and with good anchoring ability. This makes it possible to maximize both the strength of the implant element and its anchoring in the surrounding tissue.

The aspects relating to fracture mechanics are of central importance to the present invention, and for these reference is made generally to Handbook 6, edition 3, "Pulverteknik", chapter 7 CERAMICS, in particular pages 7–24 to 7–39, published by MMS (now SMS), 1995.

Other related aspects of the invention, especially with regard to biological response, are treated in the scientific literature and also, inter alia, in the following patent publications.

DE 3301122—sintering of titanium dioxide and hydroxyapatite at high temperatures where disintegration of hydroxyapatite takes place; U.S. Pat. No. 4,149,893—hot pressing in an open system of pure hydroxyapatite; U.S. Pat. No. 4,599,085 sintering and extrusion of metal with macroscopic hydroxyapatite areas—of the order of 100–500 micrometres; and EP 0 328 041—porous layer of zirconium oxide and Ca phosphate on a sintered body of zirconium oxide.

The present invention concerns high-strength, fatigue-resistant materials with maximum anchoring ability, produced by a processing technique which simplifies and at the same time extends the scope of application of surface layers, which have a favourable biological response, to different types of core materials independently of the geometry of the core material.

DESCRIPTION OF THE INVENTION

The object of the invention is to make available implant elements or other medical products made of biological material with optimum mechanical and biological properties for a wide group of materials by introduction of a specially designed surface layer onto a strong core.

The key point of the invention—based on aspects of fracture mechanics and biology—concerns the design of the material as thin layers on a core, and the method for producing these. Improved and more reliable material in terms of mechanics and biology is obtained if the following characteristics—with reference to FIGS. 1 and 2—are observed:

1) A very thin surface layer (III) with a thickness preferably of less than 5 micrometres is applied to a solid core (IV);

2) The surface layer can consist of one or more phases, depending on the application, for example a biocompatible matrix (II) and in addition a specially favourable phase (I) from the point of view of anchoring in bone. The surface layer can thus consist of either phase (I) or phase (II) or mixtures of phases (I) and (II);
3) The matrix material (II) in the surface layer preferably comprises a ceramic, for example an oxide of titanium, or a metal, while a favourable phase (I) can be of the Ca phosphate type;
4) The supporting core material (IV) consists of a metal, preferably titanium or zirconium or alloys thereof, or Co-based or Fe-based alloys—or a construction ceramic—preferably an oxide of zirconium, aluminium or titanium.

The surface layer can be applied, for example, by dipping or spraying at room temperature, and by densification in a closed system. Several thin layers can be applied one upon the other. However, the combined surface thickness is preferably less than 5 micrometres.

The above steps give the material (the product) a number of completely unique properties as set out below:
1) Application of the surface layer to an implant entails no reduction or virtually no reduction in the strength of the component compared to implants with no layers;
2) The surface layer results in good biocompatibility, and, in the case of a biologically favourable phase, anchoring with extremely good shearing forces in the contact zone between implant and bone tissue;
3) In the case of hot isostatic pressing, favourable physical anchoring of surface layer to core takes place, especially if the composition of the surface layer is chosen to be compatible with the core;
4) The low thickness of the surface layer, preferably under 5 micrometres, means that the geometry of the implant component is determined by the core material, which can thus be chosen freely. The layer can be applied to already existing commercial implants. Changes in size caused by coating can lie within given tolerances without layers. The topography of the core material can be retained. The small layer depth permits coating of different areas of a component with varying geometry (threads, elevations, grooves, holes, etc.);
5) The small thickness of the surface layer minimizes mechanical stresses in the layer and dramatically reduces the tendency towards formation of fissures;
6) Undesired chemical reactions and disintegration are prevented by means of the chosen process parameters.

FURTHER ASPECTS OF THE INVENTION

By generally keeping the particle size in the material small, and, in the case of material with more than one phase, keeping the particles (crystallites) in the phase which has the lowest fracture toughness (i.e. which is the weakest) in discrete and separated areas of a size below the critical size c in terms of fracture mechanics, instantaneous fractures can be avoided. This critical size c can be determined with the aid of the basic fracture mechanics equation $K_{IC} = Y \sigma_b c^{1/2}$ (equation 1), where $K_{Ic}$ is the fracture toughness, Y a position and shape factor, c the critical defect size, and $\sigma_b$ the breaking stress for the component. The critical defect size c varies greatly and depends on the material parameter $K_{IC}$, the said fracture toughness or critical stress intensity factor. Pure Ca phosphate the composite layer. In one embodiment according to the invention, 100% apatite is used as the surface layer.

Fractures in the surface layer can occur not only instantaneously, but also after a certain period of loading. This phenomenon, which is a type of fatigue, means that fractures can occur after a certain time at loads which are much less than the breaking strength (stress at instantaneous fracturing), even down to 20% of the stress which gives instantaneous fracturing. The tendency for these delayed fractures to occur, often called slow fissure growth, originates from the so-called stress intensity factor exponent, n, which varies greatly for different materials, from about 5–10 for pure Ca phosphate phases and glass to in excess of 100 for construction ceramics. With corrosion-resistant oxide matrix material (with high n values) present as continuous phase, which occurs at contents over 50% by volume, there is a greatly reduced tendency towards slow fissure growth. In those cases where Ca phosphates are included in the layer, the content of Ca phosphate must therefore be limited to <50% by volume.

If account is taken not only of instantaneous fractures, but also of slow fissure growth, the critical c values—and related thicknesses of surface layers—which can be calculated from equation 1 above must be further reduced. This reduction in the thickness can be calculated from the n value for the material in question and lies within the range of 4–25% of the thickness based on equation 1 for instantaneous fractures. Thus, the $K_{IC}$ value is the guiding point for critical thicknesses of the surface layer, directly as regards instantaneous fractures and indirectly as regards thicknesses related to fatigue and delayed fractures.

Equation 1 above is applicable to bulk material, where it is most used, but is also applicable to thin material. For very thin fibres and whiskers, strengths have been measured which are close to the maximum theoretical strength which can be calculated from the binding strength between the atoms involved. Calculations based on information in the literature (D. W. Richerson, Modern Ceramic Engineering, page 170, Marcel Dekker, Inc., 1992) show that equation 1 can be applied to material as thin as 50–300 Å depending on the fracture resistance, rigidity and surface energy of the material.

A minimum thickness of the surface layer means that application is made easier, especially to more complicated geometries of the core material, and that the desired tolerances can be more easily obtained. For statistical reasons, and for reasons relating directly to process technology (above all the particle sizes of the raw materials used), and for reasons relating to general design requirements, the surface layer thickness is chosen such that it exceeds the lower limit of 50–300 Å, but at the same time such that it is clearly less than the maximum permitted value based on equation 1 related to instantaneous fractures and risk of fatigue.

Slow fissure growth can be avoided, on the one hand by minimizing the possible critical defect size by minimizing the thickness of the surface layer as set out above, and, on the other hand, by reducing the stress intensity in the material by reducing the applied stress. The latter can be done by way of the chosen geometry of the component. A design stress is obtained which is judged not to be exceeded when the component is being used. Reduction of the stress intensity $K_I$ ($K_I = Y \sigma c^{1/2}$, where a and c are actual values) can generally take place in two ways, either by reducing the stress or by decreasing the defect size. For material with high $K_{IC}$ values, i.e. material with high fracture toughness and generally high fracture phases have a low fracture toughness, of the order of magnitude of 1 MPa m$^{1/2}$, which means that fractures in these phases are triggered at considerably lower stresses than in the case of phases with higher fracture toughness. Another way of expressing equation 1 above is to say that material with increased fracture toughness, $K_{IC}$, is less sensitive to defects.

A defect is an inhomogeneity in the microstructure of the material and can consist of a secondary phase, too large a particle size, a small fissure, areas which have densified differently, too large a pore size or an impurity in the material. However, for bulk material with a secondary phase, the strength first falls at secondary phase contents in excess of about 20% by volume, since contiguous areas of the poorer phase, poorer in terms of fracture mechanics, more readily occur then. Defect sizes, c, which control the strength in accordance with equation 1 above are almost exclusively within the range of 5–30 micrometres in ceramics, depending on the fracture toughness of the material.

For material present as a surface layer, there is at least one further critical aspect, namely the fact that the direction of extension of the defect is critical, and this is at right angles to the surface. In the present invention use is made of surface layers which are preferably less than 5 micrometres in the direction of their depth. This means that the size of the defect in the critical direction can be limited to be at most equal to the thickness of the surface layer. Therefore, if the thickness of the layer is limited to <c in equation (1) above for the actual layer, critical defects which give instantaneous fractures for a given stress cannot occur. This in turn means that the surface layer has greater tolerance with respect to fracture-susceptible phases such as biologically favourable Ca phosphates, even in higher contents in resistance, the stress in the component can be reduced so that the risk of fatigue is in principle eliminated. For material with low $K_{IC}$ values and susceptible to fracturing, the stress cannot be allowed to drop to the point corresponding to the threshold stress for fatigue. Instead, the stress intensity must in this case be lowered by means of dramatically reducing the defect size, which according to the invention is achieved by applying, to a solid core, a thin surface layer whose thickness is chosen such that the stress intensity does not result in the fatigue phenomenon. In summary, the critical defect size (surface layer thickness) for material with high fracture toughness can be determined directly from equation 1, while for material susceptible to fractures the critical defect size (surface layer thickness) can be calculated from the stress intensity for the chosen design stress. Two examples clearly explain the above. An aluminium oxide material has a fracture toughness of about 4 MPa m$^{1/2}$ and a breaking stress of 600 MPa and the stress intensity exponent n=100. This means that the critical defect size for instantaneous fractures is about 11 micrometres, and that the threshold stress is about 300 MPa. For hydroxyapatite with $K_{IC}$=1.1 MPam$^{1/2}$ and n=15 and the break stress 200 MPa, a critical defect size of about 13 micrometres is obtained, and a threshold stress of about 20 MPa. The design stress below 300 MPa is then permitted for aluminium oxide. With a surface layer of the aluminium oxide material having a thickness of 10 micrometres, fractures are thus prevented from occurring instantaneously or through fatigue at stresses below 300 MPa. The threshold stress of 20 MPa for hydroxyapatite is too low to be tolerated in an implant. However, the stress intensity of the material can be lowered by means of reducing the critical defect size. At the same time, a higher applied stress can be tolerated. With a critical defect size of about 1.2 micrometres for hydroxyapatite, a design stress of about 100 MPa can be tolerated without the stress intensity increasing to over 20% of the fracture toughness value. Thus, if the surface layer thickness of hydroxyapatite is maximized to 1 micrometre, a slow fissure growth can be completely avoided for a tolerable permitted design stress of 100 MPa.

Limiting the Ca phosphate phase to a maximum of 50% by volume in the surface layer does not detrimentally affect the anchoring ability since there has been found to be a non-linear relationship between anchoring ability and Ca phosphate content (apatite) in the composite. The anchoring ability of the implant element with respect to the surrounding tissue increases as the content of biologically favourable phase increases. However, the anchoring ability already reaches its maximum value at 40–50% biologically active phase. See example 1.

A further aspect which plays a central role is the production process. In this connection it has been found that a production process with exceptionally good characteristics involves hot isostatic pressing at relatively low temperatures, below those reported in the literature and in Swedish Patent 465 571. By using thin layers, compression takes place at lower temperatures than for corresponding bulk material. This in turn means that the risk of undesired reactions and disintegration is greatly reduced. Incipient disintegration can have a negative effect, on the one hand on the anchoring capacity and, on the other hand, on the resulting strength of the composite. The low process temperature also means that reaction between core material and phases in the contact zone of the surface layer with the core is largely eliminated.

Layers with thicknesses of about 0.5 micrometre can be reproducibly coated using a special spray method. In one special method, a first coating takes place with a composite layer with a lower content of biologically favourable phase, preferably <15% by volume, followed by an outer layer with higher contents. An example of a composite surface layer is titanium dioxide-apatite. When this is used for a core other than titanium, a thin layer of pure titanium dioxide can be applied as an innermost layer.

The matrix phase and the biologically favorable phase have a microstructure in which the extent of the individual particles or glass phase at right angles to the implant surface is less than 1 micrometer, preferably less than 0.4 micrometer.

Examples of the most relevant layer types are shown in FIGS. 3–4. The maximum total layer thickness is 2–5 micrometres. FIG. 3 is a general overview in which one or more layers can be used, and FIG. 4 shows typical special layers where, once again, there can be one or more surface layers.

Referring to FIGS. 3 and 4, the following labels have been used:

FIG. 3:
1) core of titanium, other metal or ceramic
2) an oxide
3) mixture of oxide and Ca phosphate phase (mostly oxide)
4) mixture of Ca phosphate phase and oxide (mostly Ca phosphate phase)
5) pure Ca phosphate phase(s)

FIG. 4:
a) titanium core 6 with surface layer 7 of titanium dioxide with varying content of hydroxyapatite
b) titanium core 6 with two layers, layer 8 consisting of titanium dioxide and Ca phosphate, and layer 9 consisting of pure Ca phosphate phase
C) titanium core 6 with three layers, layer 10 titanium dioxide, layer 11 a mixture of titanium dioxide and hydroxyapatite, layer 12 pure hydroxyapatite
d) Co—Cr core 13, with two layers, layer 14 consisting of pure titanium dioxide, layer 15 consisting of a mixture of titanium dioxide and hydroxyapatite e) core 16 of zirconium oxide, and with a layer 17 consisting of either pure hydroxyapatite or pure fluoroapatite f) core 18 of an oxide, with a layer 19 consisting of a mixture of an oxide and hydroxyapatite.

Further aspects of the invention will become clear from the following illustrative embodiments.

EXAMPLE 1

Aluminium oxide (A) manufactured by Sumitomo and hydroxyapatite (HA) manufactured by Merck were mixed in different concentrations (0, 15, 25, 45, 60, 80 and 100 % by volume of HA). The material was mixed by grinding in a ball mill for 4 days with isopropanol as solvent and with silicon nitride balls as grinding medium in a polyethyelene container. The material was densified to almost complete density, exceeding 98% of theoretical density, with the aid of hot isostatic pressing, by means of closure at about 900° C. and final densification at 1225° C. and 200 MPa pressure. Cylinders measuring 2.8 mm in diameter and about 6 mm in length were formed from the processed material, with $R_a$ value about 0.2 micrometre. The cylinders were fitted in the femurs of rabbits for 12 weeks, after which shearing forces—as a measure of the binding strength in the contact zone—were measured by the push-out test. The following table shows the strengths measured at different HA contents:

| Material | HA content % by vol. | Shearing force Mpa* | force %** |
|---|---|---|---|
| A | 0 | 2 | 10 |
| A-HA | 15 | 6 | 40 |
| A-HA | 25 | 8 | 60 |
| A-HA | 40 | 14 | >90 |
| A-HA | 45 | 15 | 100 |
| A-HA | 60 | 16 | 100 |
| A-HA | 80 | 15 | 100 |
| HA | 100 | 15 | 100 |

*Spread in data about 10% rel.
**Hydroxyapatite value set at 100%

The connection between HA content and shearing force (anchoring capacity) is not linear, but, as can be seen from the table, a maximum value is already obtained at contents below 50%. For compositions in the titanium dioxide/hydroxyapatite system, with hot isostatic pressing at 900° C., similar non-linear connections with maximum anchoring capacity are obtained within the range of 40–50% hydroxyapatite.

EXAMPLE 2

Mixtures of titanium dioxide (T) and hydroxyapatite (HA) (% by volume HA 15, 30 and 45) and pure hydroxyapatite were sprayed onto titanium metal to different mean depths, about 1, 3, 10, 30 and 50 micrometres in the densified layer. The spray-coated bodies were subjected to hot isostatic pressing at 850° C. and 160 MPa pressure for 1 hour. The processed specimens were examined under a scanning electron microscope to evaluate the microstructure and possible presence of fissures.

The result shows that a similar homogeneous microstructure is obtained independently of the layer thickness. However, the marked difference is the occurrence of surface fissures which can only be detected for composite layers exceeding 10 micrometres in average thickness. For pure HA layers, isolated surface fissures can also be seen at thicknesses of about 10 micrometres.

What is claimed is:

1. A biocompatible implant comprising:
    a core; and
    at least one surface layer, said surface layer having a thickness less than c, wherein c is defined by the equation $K_{IC} = Y\sigma c^{1/2}$, wherein $K_{IC}$ is the fracture toughness,
    Y is a constant related to position and shape factor,
    σ is the allowed stress for the material, and
    c is the critical defect size.
2. A biocompatible implant, according to claim 1, wherein said surface layer has a thickness at least 0.005 micrometers.
3. A biocompatible implant, according to claim 1, wherein said surface layer has a thickness at least 0.03 micrometers.
4. A biocompatible implant, according to claim 1, wherein said surface layer has an average thickness less than 30 micrometers.
5. A biocompatible implant, according to claim 1, wherein said surface layer has an average thickness less than 5 micrometers.
6. A biocompatible implant, according to claim 1, wherein said surface layer has an average thickness less than 10 micrometers.
7. A biocompatible implant, according to claim 1, wherein said surface layer comprises:
    a metal-ceramic matrix, wherein said ceramic is preferably in the range 30–50% by volume and wherein said ceramic includes apatitic or active glass CaPO; and
    said metal being selected from the group consisting of Ti, $TiO_2$, and other Ti compound.
8. A biocompatible implant, according to claim 7, wherein said surface layer has an average thickness less than 10 micrometers.
9. A biocompatible implant, according to claim 7, wherein said surface layer has an average thickness less than 2 micrometers.
10. A biocompatible implant, according to claim 1, wherein said surface layer comprises:
    50–100% of a biocompatible phase comprising calcium phosphate containing material, wherein the thickness of said surface layer is less than about 5 micrometers.
11. A biocompatible implant, according to claim 1, wherein the thickness of said surface layer is less than about 1 micrometer.
12. A biocompatible implant, according to claim 1, wherein said surface layer comprises:
    a corrosion-resistant matrix phase, wherein said matrix comprises a metal selected from the group consisting of Ti, $TiO_2$, and other Ti compound; and
    30–50% of a biocompatible phase wherein said biocompatible phase comprises a calcium phosphate compound selected from the group consisting of apatite, CaP biologically-active glass, and other CaP compound.
13. A biocompatible implant, according to claim 1, wherein said surface layer comprises an oxide.
14. A biocompatible implant, according to claim 13, wherein said oxide is selected from the group consisting of titanium dioxide, zirconium oxide, and tantalum oxide.
15. A biocompatible implant, according to claim 1, wherein said core comprises metal or ceramic.
16. A biocompatible implant, according to claim 1, wherein said core comprises titanium, zirconium, or alloys thereof.

17. A biocompatible implant, according to claim 16, wherein said alloys comprise Fe or Co.

18. A biocompatible implant, according to claim 1, wherein said surface layer is treated by densification.

19. A biocompatible implant, according to claim 18, wherein said densification comprises temperatures less than 1000° C.

20. A biocompatible implant, according to claim 18, wherein said densification comprises temperatures less than 900° C.

21. A biocompatible implant, according to claim 18, wherein said surface layer comprises a plurality of layers wherein for any two adjacent layers, the core-most layer comprises a lower concentration of said biocompatible phase.

22. A biocompatible implant, according to claim 12, wherein said biocompatible phase comprises:
  a plurality of particles embedded in said corrosion-resistant matrix phase, wherein each of said particles comprises:
  an axis, perpendicular to a surface of said core, wherein the length of said axis is less than 1 micrometer.

23. A biocompatible implant, according to claim 12, wherein the length of said axis is less than 0.4 micrometer.

* * * * *